US012378599B2

(12) United States Patent
Dahl et al.

(10) Patent No.: US 12,378,599 B2
(45) Date of Patent: *Aug. 5, 2025

(54) PROBE SET FOR ANALYZING A DNA SAMPLE AND METHOD FOR USING THE SAME

(71) Applicant: Vanadis Diagnostics, Sollentuna (SE)

(72) Inventors: Carl Oscar Fredrik Dahl, Sigtuna (SE); Olof John Ericsson, Uppsala (SE); Filip Karlsson, Solna (SE); Fredrik Roos, Stockholm (SE)

(73) Assignee: VANADIS DIAGNOSTICS, Sollentuna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/099,913

(22) Filed: Jan. 20, 2023

(65) Prior Publication Data

US 2023/0159991 A1    May 25, 2023

Related U.S. Application Data

(63) Continuation of application No. 17/039,490, filed on Sep. 30, 2020, now Pat. No. 11,591,639, which is a continuation of application No. 16/679,098, filed on Nov. 8, 2019, now Pat. No. 10,822,640, which is a continuation of application No. 15/268,322, filed on Sep. 16, 2016, now Pat. No. 10,508,300.

(60) Provisional application No. 62/220,746, filed on Sep. 18, 2015.

(51) Int. Cl.
C12N 15/11    (2006.01)
C12Q 1/682    (2018.01)
C12Q 1/6858    (2018.01)

(52) U.S. Cl.
CPC .......... *C12Q 1/682* (2013.01); *C12Q 1/6858* (2013.01)

(58) Field of Classification Search
None
See application file for complete search history.

(56) References Cited

U.S. PATENT DOCUMENTS

| | | | |
|---|---|---|---|
| 5,854,033 A | 12/1998 | Lizardi et al. | |
| 10,508,300 B2 * | 12/2019 | Dahl | C12Q 1/682 |
| 10,822,640 B2 * | 11/2020 | Dahl | C12Q 1/682 |
| 11,591,639 B2 * | 2/2023 | Dahl | C12Q 1/6858 |
| 2003/0022167 A1 | 1/2003 | Alsmadi et al. | |
| 2004/0166514 A1 | 8/2004 | Puskas | |
| 2007/0087355 A1 | 4/2007 | Barrett | |
| 2008/0199916 A1 | 8/2008 | Zheng et al. | |
| 2009/0004666 A1 | 1/2009 | Tanabe et al. | |
| 2009/0004701 A1 | 1/2009 | Faham et al. | |
| 2009/0156412 A1 | 6/2009 | Boyce, IV et al. | |
| 2012/0003675 A1 | 1/2012 | Retterer et al. | |
| 2012/0029056 A1 | 2/2012 | Alevizos et al. | |
| 2012/0157322 A1 | 6/2012 | Myllykangas et al. | |
| 2014/0242577 A1 | 8/2014 | Peter | |
| 2015/0307875 A1 | 10/2015 | Happe et al. | |
| 2015/0368639 A1 * | 12/2015 | Gill | G16B 30/00 506/26 |
| 2016/0017425 A1 | 1/2016 | Ruvolo et al. | |

FOREIGN PATENT DOCUMENTS

| | | |
|---|---|---|
| CN | 102344961 A | 2/2012 |
| CN | 104099409 A | 10/2014 |
| CN | 104854246 A | 8/2015 |
| CN | 104870654 | 8/2015 |
| EP | 2653559 | 10/2013 |
| GB | 2492042 | 12/2012 |
| JP | 2012522508 | 9/2012 |
| JP | 2013544498 | 12/2013 |
| JP | 2016537990 | 12/2016 |
| WO | 9710364 | 3/1997 |
| WO | 2001094625 | 12/2001 |
| WO | 2003044216 | 5/2003 |
| WO | 2004/057017 | 7/2004 |
| WO | 2005047547 | 5/2005 |
| WO | 2005111236 | 11/2005 |
| WO | 2009029742 | 3/2009 |
| WO | 2011009941 | 1/2011 |
| WO | 2011142836 | 11/2011 |
| WO | 2012019200 | 2/2012 |

(Continued)

OTHER PUBLICATIONS

Chen et al (Genomics 38:30-7) (Year: 1996).*
Shan et al (Nature Genetics 19:91-3) (Year: 1998).*
Dahl et al., "Multiplex amplification enabled by selective circularization of large sets of genomic DNA fragments" Nucleic Acids Res, Apr. 2005, p. e71, vol. 33, No. 8.
Fredriksson et al., "Multiplex amplification of all coding sequences within 10 cancer genes by Gene-Collector" Nucleic Acids Res, Apr. 2007, p. e47, vol. 35, No. 7.
Guo et al., "Simultaneous Detection of Trisomies 13, 18, and 21 with Multiplex Litigation-Dependent Probe Amplification-Based Real-Time PCR" Clinical Chemistry, Sep. 2010, pp. 1451-1459, vol. 56, No. 9.
Hardenbol et al., "Multiplexed genotyping with sequence-tagged molecular inversion probes" Nat Biotechnol, Jun. 2003, pp. 673-678, vol. 21, No. 6.

(Continued)

Primary Examiner — Christopher M Gross
(74) Attorney, Agent, or Firm — James S. Keddie; Bozicevic, Field & Francis LLP

(57) ABSTRACT

This disclosure provides, inter alia, a probe system probe system for analyzing a nucleic acid sample. In some embodiments, the probe system may comprise: a set of identifier oligonucleotides of sequence B, a set of splint oligonucleotides of formula X'-A'-B'-Z', wherein sequence A' is complementary to a genomic fragment and sequence B' is complementary to at least one member of the set of identifier oligonucleotides, and one or more probe sequences comprising X and Z. Each splint oligonucleotide is capable of hybridizing to the probe sequences, a member of the set of identifier oligonucleotides and a genomic fragment, thereby producing a ligatable complex of formula X-A-B-Z. The probe system can be used to identify a chromosome aneuploidy in cell free DNA, for example.

12 Claims, 8 Drawing Sheets

(56) References Cited

FOREIGN PATENT DOCUMENTS

| WO | WO12019198  | 2/2012  |
|----|-------------|---------|
| WO | 2013079649  | 6/2013  |
| WO | 2014165267  | 10/2014 |
| WO | 2015083001  | 6/2015  |
| WO | 2015083002  | 6/2015  |
| WO | 2016024182  | 2/2016  |
| WO | 2016174649  | 11/2016 |
| WO | 2017/046775 | 3/2017  |

OTHER PUBLICATIONS

Hardenbol et al., "Highly multiplexed molecular inversion probe genotyping: over 10,000 targeted SNP's genotyped In a single tube assay" Genome Res, Feb. 2005, pp. 269-275, vol. 15, No. 2.

Marciniak et al., "Coupled rolling circle amplification loop-mediated amplification for rapid detection of short DNA sequences" BioTechniques, Sep. 2008, pp. 275-280, vol. 45, No. 3.

Shen et al., "Multiplex target capture with double-stranded DNA probes" Genome Med, 2013, p. 50, vol. 5, No. 5.

Amann, et al., "Combination of 16S rRNA-Targeted Oligonucleotide Probes with Flow Cytometry for Analyzing Mixed Microbial Populations", Applied and Environmental Microbiology, 1990, 56(6): 1919-1925.

Eriksson, et al., "Multiplex and quantifiable detection of nucleic acid from pathogenic fungi using padlock probes, generic real time PCR and specific suspension array readout", Journal of Microbiological Methods, 2009, 78: 195-202.

Nilsson, et al., "Real-time monitoring of rolling-circle amplification using a modified molecular beacon design", Nucleic Acids Research, 2002, 30(14): e66.

Zhou, et al., "Two-color, rolling-circle amplification on antibody microarrays for sensitive, multiplexed serum-protein measurements", Genome Biology, 2004, 5:R28.

Lizardi et al., "Mutation detection and single-molecule counting using isothermal rolling-circle amplification", Nature Genetics, 1998, 19(3):225-232.

Database EMBL [Online], "Human centromeric alphoid repeat DNA unit (h3)", 1986, retrieved from EBI accession No. EM_STD:X02953 Database accession No. X02953.

International Search Report and Written Opinion of the International Searching Authority issued for International Application No. PCT/IB2016/055558, Dec. 5, 2016.

* cited by examiner

In the top strand:
-sequence A is a fragment of genomic DNA;
-sequence B identifies the locus, e.g., the chromosome, from which the adjacent fragment of genomic DNA is derived;
-sequences X and Z are probe sequences.

PROBE SET FOR ANALYZING A DNA SAMPLE AND METHOD FOR USING THE SAME

CROSS-REFERENCING

This application is a continuation of U.S. application Ser. No. 17/039,490, filed on Sep. 30, 2020, which is a continuation of U.S. application Ser. No. 16/679,098, filed on Nov. 8, 2019, now issued as U.S. Pat. No. 10,822,640, which is a continuation of U.S. application Ser. No. 15/268,322, filed on Sep. 16, 2016, now issued as U.S. Pat. No. 10,508,300, which claims the benefit of provisional application Ser. No. 62/220,746, filed on Sep. 18, 2015, which applications are incorporated by reference herein in their entirety.

BACKGROUND

Cell free DNA ("cfDNA") can be analyzed to provide a prognosis, diagnosis or a prediction of a response to a treatment for a variety of diseases and conditions, including various cancers, transplant failure or success, inflammatory diseases, infectious disease and fetal aneuploidy.

Cell-free fetal DNA (cffDNA) is present in the blood of a pregnant female. This discovery led to the possibility of performing non-invasive prenatal testing (NIPT) of a fetus using a blood sample from the pregnant female. Invasive prenatal tests (e.g., amniocentesis or chorionic villi sampling (CVS)) can be stressful for the mother and some believe such procedures may increase the risk of miscarriage. NIPT can provide information related to a variety of genetic defects, including Down syndrome (trisomy chromosome 21), Patau syndrome (trisomy 13), and Edwards syndrome (trisomy 18). Such methods should be highly robust as a false positive may lead to unnecessary medical procedures, and a false negative may deprive the expectant mother of understanding the available medical options.

There are many technical hurdles associated with implementing a non-invasive prenatal test on a clinical scale. For example, many NIPT efforts have focused on the analysis of cffDNA to identify copy number changes in particular sequences (e.g., sequences from chromosome 21). However, such methods are difficult to implement in a robust way because, in part, the vast majority of cfDNA in a blood sample is maternal in origin and in many cases only a very small amount (e.g., on average ~10% and down to about 3%) is from the fetus. For example, the presence or absence of an extra copy of a chromosome (such as chromosome 21) in the fetus may be determined by comparing the copy number of sequences corresponding to chromosome 21 to the copy number of sequences corresponding to an autosomal chromosome. While such methods sound attractive, they are in fact challenging because the fractional concentration of fetal DNA relative to maternal DNA in maternal blood can be as low as 3%. As such, for every 1000 sequences corresponding chromosome 21 that are in the maternal bloodstream, only a small percentage of those sequences (e.g., 30 sequences if the fetal fraction is 3%) are from the fetus. Thus, an extra copy of a chromosome in the fetus will only lead to a relatively small increase in the number of sequences corresponding to that chromosome in the maternal bloodstream. For example, if the fetal fraction is 4, fetal trisomy 21 will only lead to a 1.5% increase in the number of fragments corresponding to chromosome 21 in the maternal bloodstream. As a result of this problem, statistical rigor can only be achieved by counting large numbers of sequences corresponding to a chromosomal region that is suspected of having a copy number difference (e.g., at least 1,000 and sometimes at least 5,000 or more sequences) and comparing that number to a similar number for another chromosomal region that is not suspected of having a copy number difference. Being able to consistently and accurately count fragments is paramount to the success of many NIPT methods.

Some NIPT methods use polymerase chain reaction (PCR) to amplify the DNA. PCR is widely used, but it suffers from various limitations that can negatively affect the accuracy of the results. PCR can introduce sequence artifacts and create amplification bias in a sample. PCR sequence artifacts are errors introduced into the DNA sequence of the PCR amplified product by the PCR reaction. PCR sequence artifacts can be caused by various events, such as by the formation of chimeric molecules (e.g., two different pieces of DNA joined end to end), the formation of heteroduplex DNA (e.g., the hybridization of two different DNA molecules to each other) and by errors made by the amplification enzyme (e.g., by Taq DNA polymerase placing a mismatched nucleotide onto the DNA template). Sequence bias from PCR is a skewing of the distribution of PCR products compared to the original sample. PCR sequence bias can be caused by various events, such as intrinsic differences in the amplification efficiency of templates or inhibition of amplification due to self-annealing of DNA templates. PCR errors result in an unequal amplification of the different DNA molecules so that the amplified sample is no longer representative of the original sample. PCR is also notoriously sensitive to exogenous DNA contamination from the environment. Due to the exponential amplification of DNA during PCR, even very small amounts of exogenous DNA contamination in a PCR reaction can lead to highly inaccurate results. Exogenous DNA contamination can be introduced from aerosolized droplets floating in the air or can be transferred into a reaction from contaminated equipment.

Use of rolling-circle amplification (RCA) to analyze cfDNA in maternal blood avoids many of the problems associated with PCR. However, RCA products are not very easy to quantify in a way that provides statistical robustness. At a practical level, although the absolute numbers of products in an RCA reaction may be sufficiently high to provide statistical robustness, different RCA products may be amplified and detected at different efficiencies and, as such, consistently detecting tens or hundreds of thousands of RCA products evenly has been challenging.

SUMMARY

Described herein, among other things, is a system of probes for analyzing a nucleic acid sample. The probes may be designed in such a way that they can be ligated to target fragments of genomic DNA (also referred to herein as "target sequences" or merely "fragments") from different loci (e.g., different chromosomes) to produce circular DNA molecules. The circular DNA molecules, even if they contain fragments from different chromosomes, all contain the same "backbone" sequence. Further, in some embodiments, all of the circular DNA molecules that contain a fragment from the same locus contain the same locus-specific identifier sequence, i.e., a locus-specific barcode. In these embodiments, the circular DNA molecules can be amplified using a primer that hybridizes to a sequence in the backbone, and the locus from which the cloned fragment is derived can be detected by hybridizing the RCA products to a labeled oligonucleotide that hybridizes to the locus-specific identifier sequence. As would be apparent, this embodiment of the method can be multiplexed using multiple locus-specific identifier sequences and distinguishably-labeled oligonucleotides that hybridize to those sequences. Because all of the circular products have the same backbone and only differ from one another by the sequence of the cloned fragment and the locus-specific barcode, the RCA products amplified from those products amplified consistently, and the locus to which those RCA products correspond can be detected with accuracy. A method that employs the probe system, as well as a kit for practicing the same, are also provided.

As will be discussed in greater detail below, in certain cases the method may be used to detect chromosome abnormalities (e.g., trisomy 21) in a fetus using a sample of cfDNA from a pregnant female carrying the fetus.

A probe system for analyzing a nucleic acid sample is provided. In some embodiments, the probe system may comprise: (a) a set of identifier oligonucleotides of sequence B; (b) a set of splint oligonucleotides of formula X'-A'-B'-Z', wherein: within the set: (i) sequences A' and B' vary, and (ii) sequences X' and Z' are different from each other and are not variable; and, within each splint oligonucleotide: (i) sequence A' is complementary to a genomic fragment of the nucleic acid sample and (ii) sequence B' is complementary to at least one member of the set of identifier oligonucleotides; and (c) one or more probe sequences comprising X and Z, where sequences X and Z are not variable and hybridize to sequences X' and Z'; where each splint oligonucleotide is capable of hybridizing to: (i) the probe sequences, (ii) a member of the set of identifier oligonucleotides and, (iii) the genomic fragment, thereby producing a ligatable complex of formula X-A-B-Z. In some embodiments, the different identifier oligonucleotides and their complementary sequences B' identify different chromosomes, e.g., chromosomes 21, 18 and 13.

In some embodiments, the set of identifier oligonucleotides may comprise at least two (e.g., two, three or four or more) different B sequence identifier oligonucleotides and, within the set of splint oligonucleotides, there are at least 100 different A' sequences and at least two different B' sequences that are complementary to at least two different identifier oligonucleotides.

In some embodiments, each identifier oligonucleotide or its complementary B' sequence in a splint oligonucleotide may correspond to the genomic fragment.

In some embodiments, each identifier oligonucleotide or its complementary B' sequence in a splint oligonucleotide may indicate a locus in a genome from which the genomic fragment is derived.

In some embodiments, each identifier oligonucleotide or its complementary B' sequence in a splint oligonucleotide may indicate the chromosome from which the genomic fragment is derived.

In some embodiments, the genomic fragment is from a mammalian genome.

In some embodiments, each identifier oligonucleotide or its complementary B' sequence in a splint oligonucleotide may identify one or more of chromosome 21, chromosome 18 and chromosome 13.

In some embodiments, the genomic fragment may be a restriction fragment.

In some embodiments, the one or more probe sequences of (c) may further comprise an oligonucleotide comprising sequence Y, and wherein the ligatable complex is linear.

In some embodiments, the probe system may further comprise a pair of PCR primers that hybridize to the one or more probes of (c).

In some embodiments, the one or more probe sequences of (c) may comprise a backbone probe of formula X-Y-Z, where Y comprises an oligonucleotide sequence, such that the ligatable complex is a circular ligatable complex of formula X-A-B-Z-Y, where sequence Y joins sequences X and Z.

In some embodiments, the probe system may further comprise a rolling circle amplification primer that hybridizes to a sequence in the backbone probe.

In some embodiments, the probe system may further comprise (A) a rolling circle amplification primer that hybridizes a sequence to the backbone probe; and (B) up to four distinguishably labeled detection oligonucleotides, wherein each of the distinguishable labeled detection oligonucleotides hybridizes to a B' sequence.

A method of sample analysis is also provided. In some embodiments, the method may comprise: (a) hybridizing any embodiment of the probe system summarized above with a test genomic sample that comprises genomic fragments to produce ligatable complexes of formula X-A-B-Z; (b) ligating the ligatable complexes to produce product DNA molecules of formula X-A-B-Z; and (c) counting the product DNA molecules corresponding to each locus identifier of sequence B.

In some embodiments, the counting may be done by sequencing product DNA molecules, or amplification products thereof, to produce sequence reads, and counting the number of sequence reads comprising each sequence of B or complement thereof.

In some embodiments, the product DNA molecules may be circular, and the counting may comprise amplifying the product DNA molecules by rolling circle amplification, and counting the number amplification products comprising each sequence of B or complement thereof. In these embodiments, the method may comprise labelling the RCA products using distinguishably labeled probes that hybridize to sequence B', and the counting is done by counting the number of RCA products for each distinguishable label.

In some embodiments, the method may comprise: i. depositing the RCA products on a planar support; and ii. counting the number of the individual labeled RCA products in an area of the support. In these embodiments, the support may be a glass slide or a porous transparent capillary membrane, for example.

In some embodiments, the different sequences of B and their complementary sequences B' identify different chromosomes, and the method further comprises comparing the number of product DNA molecules comprising a first sequence of either B or B' to the number of product DNA molecules comprising a second sequence of either B or B' to determine if the genomic sample has an aneuploidy.

In some embodiments, the method may comprise comparing the counting results of step (c) with the counting results obtained from one or more reference samples.

In some embodiments, the test genomic sample may be from a patient that is suspected or at risk of having a disease or condition, and the counting results of step (c) provides an indication of whether the patient, or fetus thereof, has the disease or condition.

In some embodiments, the disease or condition may be a cancer, an infectious disease, an inflammatory disease, a transplant rejection, or a trisomy.

In some embodiments, the fragments are restriction fragments.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
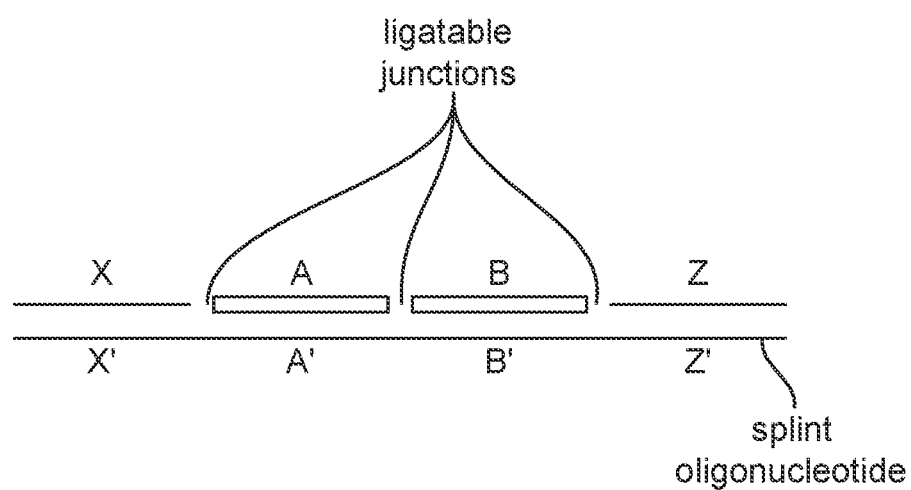
FIG. 1 schematically illustrates some of the features of the present probe system.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; and, amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "primer" as used herein refers to an oligonucleotide that is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be single-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence or fragment, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42C in 50% formamide, 5× SSC, 5× Denhardt's solution, 0.5% SDS and 100 ug/ml denatured carrier DNA followed by washing two times in 2× SSC and 0.5% SDS at room temperature and two additional times in 0.1×SSC and 0.5% SDS at 42° C. The term "barcode sequence" or "molecular barcode", as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide. Barcode sequences may vary widely in size and composition; the following references provide guidance for selecting sets of barcode sequences appropriate for particular embodiments: Casbon (Nuc. Acids Res. 2011, 22 e81), Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by, e.g., Illumina, Life Technologies, and Roche etc. Next-generation sequencing methods may also include nanopore sequencing methods or electronic-detection based methods such as, e.g., Ion Torrent technology commercialized by Life Technologies.

The term "duplex," or "duplexed," as used herein, describes two complementary polynucleotides that are base-paired, i.e., hybridized together.

The terms "determining," "measuring," "evaluating," "assessing," "assaying," and "analyzing" are used interchangeably herein to refer to forms of measurement, and include determining if an element is present or not. These terms include both quantitative and/or qualitative determinations. Assessing may be relative or absolute.

The term "affinity tag", as used herein, refers to moiety that can be used to separate a molecule to which the affinity tag is attached from other molecules that do not contain the affinity tag. An "affinity tag" is a member of a specific binding pair, i.e. two molecules where one of the molecules through chemical or physical means specifically binds to the other molecule. The complementary member of the specific binding pair, referred to herein as a "capture agent" may be immobilized (e.g., to a chromatography support, a bead or a planar surface) to produce an affinity chromatography support that specifically binds the affinity tag. In other words, an "affinity tag" may bind to a "capture agent", where the affinity tag specifically binds to the capture agent, thereby facilitating the separation of the molecule to which the affinity tag is attached from other molecules that do not contain the affinity tag.

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12.

The term "terminal nucleotide", as used herein, refers to the nucleotide at either the 5' or the 3' end of a nucleic acid molecule. The nucleic acid molecule may be in double-stranded form (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

The terms "plurality", "set" and "population" are used interchangeably to refer to something that contains at least 2 members. In certain cases, a plurality may have at least 10, at least 100, at least 100, at least 10,000, at least 100,000, at least $10^6$, at least $10^7$, at least $10^8$ or at least $10^9$ or more members.

The term "digesting" is intended to indicate a process by which a nucleic acid is cleaved by a restriction enzyme. In order to digest a nucleic acid, a restriction enzyme and a nucleic acid containing a recognition site for the restriction enzyme are contacted under conditions suitable for the restriction enzyme to work. Conditions suitable for activity of commercially available restriction enzymes are known, and supplied with those enzymes upon purchase.

An "oligonucleotide binding site" refers to a site to which an oligonucleotide hybridizes in a target polynucleotide or fragment. If an oligonucleotide "provides" a binding site for a primer, then the primer may hybridize to that oligonucleotide or its complement.

The term "separating", as used herein, refers to physical separation of two elements (e.g., by size or affinity, etc.) as well as degradation of one element, leaving the other intact.

The term "reference chromosomal region," as used herein refers to a chromosomal region of known nucleotide sequence, e.g. a chromosomal region whose sequence is deposited at NCBI's Genbank database or other databases, for example.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "covalently linking" refers to the production of a covalent linkage between two separate molecules, e.g., the top and bottom strands of a double stranded nucleic acid. Ligating is a type of covalent linking.

The term "denaturing," as used herein, refers to the separation of at least a portion of the base pairs of a nucleic acid duplex by placing the duplex in suitable denaturing conditions.

Denaturing conditions are well known in the art. In one embodiment, in order to denature a nucleic acid duplex, the duplex may be exposed to a temperature that is above the melting temperature of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). Nucleic acids may also be denatured chemically (e.g., using urea or NaOH).

As used herein, the term "label" refers to any atom or molecule that can be used to provide a detectable (preferably quantifiable) effect, and that can be attached to a nucleic acid or protein. Labels include but are not limited to dyes and radiolabels such as $^{32}P$; binding moieties such as biotin; haptens such as digoxigenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of a nucleic acid or a protein sequence, so long as the sequence comprising the label is detectable.

The terms "labeled oligonucleotide" and "labeled probe" as used herein, refer to an oligonucleotide that has an affinity tag (e.g., a biotin moiety), an oligonucleotide modified with atoms or groups enabling separation or detection (e.g., bromo-deoxyuridine, or colloidal gold particles conferring different density), and an oligonucleotide modified with or an optically detectable label (e.g., a fluorescence or another type of light emitting label). Oligonucleotides that contain only naturally occurring nucleotides are not labeled oligonucleotides.

The term "extending", as used herein, refers to the extension of a primer by the addition of nucleotides using a polymerase. If a primer that is annealed to a nucleic acid is extended, the nucleic acid acts as a template for an extension reaction.

As used herein, the term "respective ends", in the phrase "ligating a first and second oligonucleotides to the respective ends of a fragment" is intended to mean that one oligonucleotide is added to one end of the fragment and another oligonucleotide is added to the other end of the target fragment.

As used herein, the term "ligatably adjacent" in the context of two oligonucleotide sequences that are ligatably adjacent to one another, means that there are no intervening nucleotides between two oligonucleotides and they can be ligated to one another.

As used herein, the term "splint oligonucleotide", as used herein, refers to an oligonucleotide that, when hybridized to two or more other polynucleotides, acts as a "splint" to position the polynucleotides next to one another so that they can be ligated together, as illustrated in FIG. 1.

As used herein, the term "a circular nucleic acid molecule" refers to a strand that is in the form of a closed circle that has no free 3' or 5' ends.

The term "corresponds to" and grammatical equivalents, e.g., "corresponding", as used herein refers to a specific relationship between the elements to which the term refers. For example, an RCA that corresponds to a sequence in a genome contains the same nucleotide sequence as the sequence in the genome.

Certain polynucleotides described herein may be referred by a formula (e.g., "X'-A'-B'-Z'"). Unless otherwise indicated the polynucleotides defined by a formula may be oriented in the 5' to 3' direction or the 5' to 3' direction. For example, polynucleotides defined by the formula "X'-A'-B'-Z'" may be "5' X' A' B' Z' 3'" or "3' X' A' B' Z' 5'". The components of the formula, e.g., "A", "X" and "B", etc., refer to separately definable sequences of nucleotides within a polynucleotide, where, unless implicit from the context (e.g., in the case of a "ligatable" complex of a particular formula), the sequences are linked together covalently such that a polynucleotide described by a formula is a single molecule. In many cases the components of the formula are immediately adjacent to one another in the single molecule. Following convention, the complement of a sequence shown in a formula will be indicated with a prime (') such that the complement of sequence "A" will be "A'". Moreover, unless otherwise indicated or implicit from the context, a polynucleotide defined by a formula may have additional sequence, a primer binding site, a molecular barcode, a promoter, or a spacer, etc., at its 3' end, its 5' end or both the 3' and 5' ends. If a polynucleotide defined by a formula is described as being circular then the ends of those molecules are joined together, either directly or indirectly. For example, in the case of circular complexes of formula X-A-B-Z-Y, then the 5' end of the molecule is joined, directly or indirectly, to 3' end of the molecule to produce a circle. As would be apparent, the various component sequences of a polynucleotide (e.g., A, B, C, X, Y, Z, etc.) may independently be of any desired length as long as they capable of performing the desired function (e.g., hybridizing to another sequence). For example, the various component sequences of a polynucleotide may independently have a length in the range of 8-80 nucleotides, e.g., 10-50 nucleotides or 12-30 nucleotides.

The term "ligatable complex", e.g., of formula X-A-B-Z, refers to a complex in which the various oligonucleotides are ligatably adjacent to one another (in a circular or linear form), held together by a splint oligonucleotide, as shown in FIG. 1.

The term "ligatable circular complex", e.g., of formula X-A-B-Z-Y, refers to a circular complex in which the various oligonucleotides are ligatably adjacent to one another in a circle, held together by a splint oligonucleotide.

The terms "locus" "genomic locus" as used herein, refer to a defined region of a genome, e.g., an animal or plant genome such as the genome of a human, monkey, rat, fish or insect or plant. A locus can be a region of a chromosome that is as short as a 100 kb, and can be as long as a chromosome arm or an entire chromosome.

The terms "first locus" and "second locus" refer to different loci, i.e., different regions in a genome, e.g., different chromosome arms or different chromosomes.

The terms "fragments of a locus" refers to a population of defined fragments (which may be made using a restriction enzyme or by re-programming an RNA-guided endonuclease such as CAS9) of a particular locus. Not all fragments of a locus need to be analyzed. Because the sequences of various genomes have been published, design of oligonucleotides that hybridize to a fragment of a locus is routine.

The term "complementary to a fragment" refers to a sequence that is complementary to a strand (either the top or the bottom strand) of a fragment.

The term "genomic sequence", as used herein, refers to a sequence that occurs in a genome.

The term "variable", in the context of two or more nucleic acid sequences that are variable, refers to two or more nucleic acids that have different sequences of nucleotides relative to one another. In other words, if the polynucleotides of a population have a variable sequence or a particular sequence "varies", then the nucleotide sequence of the polynucleotide molecules of the population varies from molecule to molecule. The term "variable" is not to be read to require that every molecule in a population has a different sequence to the other molecules in a population.

If two nucleic acids (e.g., sequences A and A') are "complementary", they hybridize with one another under high stringency conditions. In many cases, two sequences that are complementary have at least 10, e.g., at least 12, at least 15, at least 20 or at least 25 nucleotides of complementarity and in certain cases may have one, two or three non-complementary bases.

The term "identifies", in the context of a sequence that identifies a locus, refers to a molecular barcode is unique for the locus. Such a sequence is not from the locus itself, but rather it is a molecular barcode—usually having a sequence that is not present in the sample being analyzed—that is added to the fragments of a locus that are being analyzed and that identifies those fragments as being from the locus. For example, if fragments from a first locus are ligated to a first identifier sequence and fragments from a second locus are ligated to a second identifier sequence, then the source of those fragments (the locus to which they correspond) can be determined by detecting which identifier sequence has been ligated to those fragments.

The term "inverted orientation" in the context of two sequences that hybridize to other sequences in an inverted orientation, refers to a structure in which the 5' and 3' ends of one of the sequences are hybridized to the other in a way in which the ends are facing one another, as illustrated at the top of FIG. 3B.

As used herein, the term "rolling circle amplification" or "RCA" for short refers to an isothermal amplification that generates linear concatemerized copies of a circular nucleic acid template using a strand-displacing polymerase. RCA is well known in the molecular biology arts and is described in a variety of publications including, but not limited to Lizardi et al (Nat. Genet. 1998 19:225-232), Schweitzer et al (Proc. Natl. Acad. Sci. 2000 97:10113-10119), Wiltshire et al (Clin. Chem. 2000 46:1990-1993) and Schweitzer et al (Curr. Opin. Biotech 2001 12:21-27), which are incorporated by reference herein.

As used herein, the term "rolling circle amplification products" refers to the concatamerized products of a rolling circle amplification reaction. As used herein, the term "fluorescently labeled rolling circle amplification products" refers to rolling circle amplification products that have been fluorescently labeled by, e.g., hybridizing a fluorescently labeled oligonucleotide to the rolling circle amplification products or other means (e.g., by incorporating a fluorescent nucleotide into the product during amplification).

As used herein, the term "area", in the context of an area of a support or an area of an image, refers to a contiguous or non-contiguous area. For example, if a method involves counting the number of labeled RCA products in an area, the area in which the RCA products are counted may be a single, contiguous space or multiple non-contiguous spaces.

As used herein, the term "imaging" refers to a process by which optical signals from the surface of an object are detected and stored as data in association with a location (i.e., a "pixel"). A digital image of the object can be reconstructed from this data. An area of a support may be imaged using a single image or one or more images.

As used herein, the term "individual labeled RCA products" refers to individual RCA molecules that are labeled.

As used herein, the term "counting" refers to determining the number of individual objects in a greater collection. "Counting" requires detecting separate signals from individual objects in a plurality (not a collective signal from the plurality of objects) and then determining how many objects there are in the plurality by counting the individual signals. In the context of the present method, "counting" is done by determining the number of individual signals in an array of signals.

As used herein, the term "array" with reference to an array of RCA products refers to a collection of single RCA products on a planar surface, where the RCA products are spatially separated from one another on the plane of the surface (to the extent allowed by Poisson distribution if the array is truly random). A "random" array is an array wherein the elements, e.g., RCA products, are distributed on the surface of a substrate at positions that are not predetermined. In some cases, the distribution of RCA products on a random array may be described by Poisson statistics, such that, e.g., the distribution of distances between RCA products of a random array is approximated by a Poisson distribution.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Probe Compositions

Some embodiments of the probe system may comprise: (a) a set of identifier oligonucleotides of sequence B; (b) a set of splint oligonucleotides of formula X'-A'-B'-Z', wherein: within the set: (i) sequences A' and B' vary, and (ii) sequences X' and Z' are different from each other and are not variable; and, within each splint oligonucleotide: (i) sequence A' is complementary to a genomic fragment of the nucleic acid sample and (ii) sequence B' is complementary to at least one member of the set of identifier oligonucleotides; and (c) one or more probe sequences comprising X and Z, where sequences X and Z are not variable and hybridize to sequences X' and Z'; where each splint oligonucleotide is capable of hybridizing to: (i) the probe sequences, (ii) a member of the set of identifier oligonucleotides and, (iii) the genomic fragment, thereby producing a ligatable complex of formula X-A-B-Z. As will be described in greater detail below, in some embodiments the different identifier oligonucleotides and their complementary sequences B' identify different chromosomes, e.g., chromosomes 21, 18 and 13.

Figure 2:
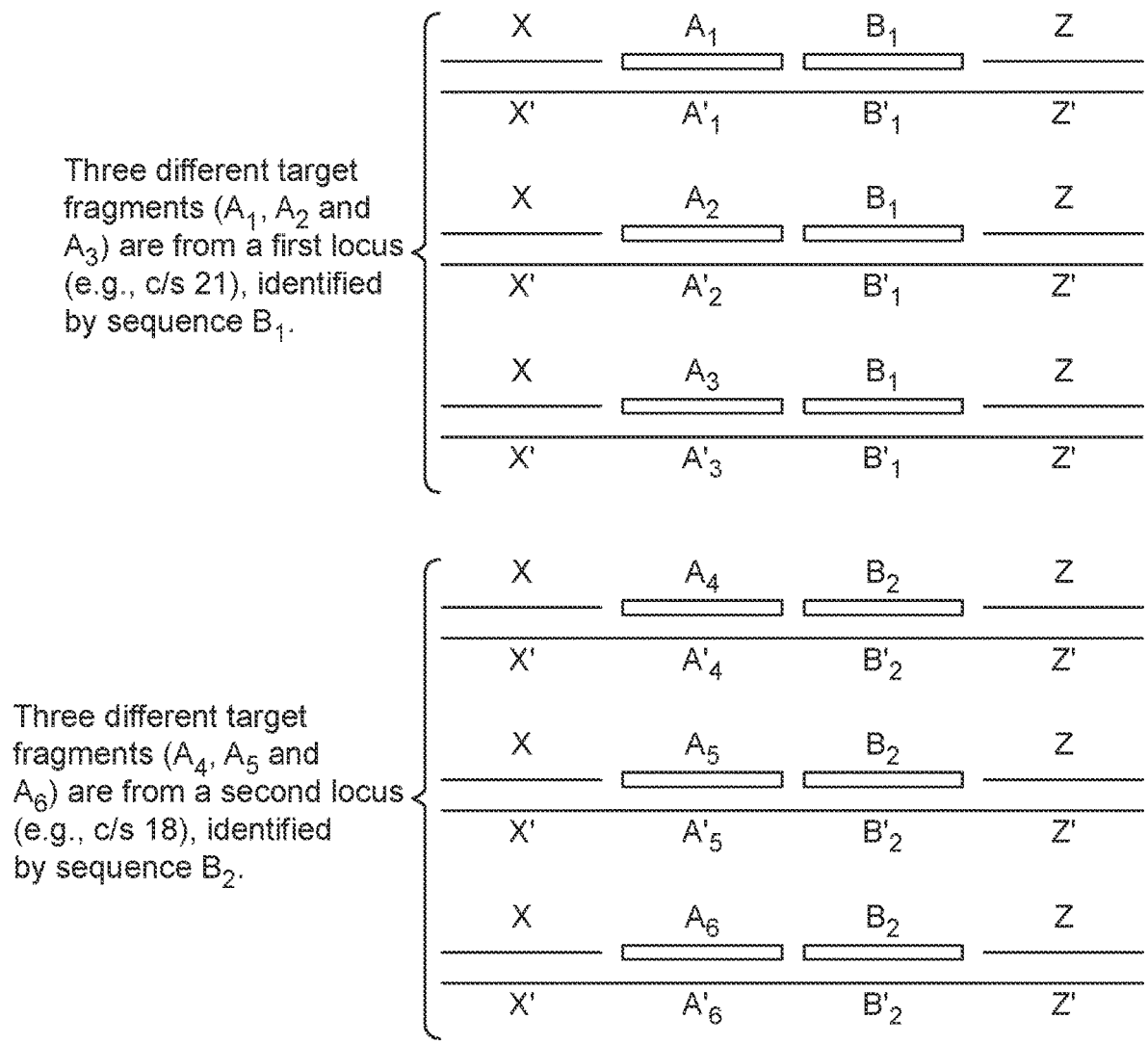
FIG. 2 schematically illustrates how sequence B serves to identify the locus of sequence A.

FIG. 1 shows the ligatable complex of formula X-A-B-Z, which structure characterizes the present probe system. As shown in FIG. 1, in the complex sequences X, A, B and Z are ligatably adjacent to one another, held in position by a splint oligonucleotide. As noted in FIG. 1, sequence A is a target fragment of a genome (e.g., a strand of a restriction fragment), and sequence B identifies the locus (e.g., a particular region on a chromosome, a particular chromosome arm or a particular chromosome, etc.) from which the adjacent sequence A is derived. The relationship between sequences A and B is illustrated in FIG. 2, which illustrates a simple probe set, hybridized to various genomic fragments ($A_1$ to $A_6$). As shown in FIG. 2, the genomic fragments in the top three complexes (of sequence $A_1$, $A_2$, and $A_3$) are from a first locus (e.g., chromosome 21) and the genomic fragments in the bottom three complexes (of sequence $A_4$, $A_5$, and $A_6$) are from a second locus (e.g., chromosome 18). The locus from which the genomic fragments in the top three complexes is derived is identified by a single sequence ($B_1$), and the locus from which the genomic fragments in the bottom three complexes is derived is identified by a different sequence ($B_2$). Sequence X and Z are the same in all illustrated complexes.

As would be apparent, the set of splint oligonucleotides can be as complex as desired and, in some embodiments, sequence A' may have a complexity of at least 100, at least 1,000, at least 5,000, at least 10,000 or at least 50,000 or more, meaning that the splint oligonucleotides can, collectively, hybridize to at least 100, at least 1,000, at least 5,000, at least 10,000 or at least 50,000 or more fragments of genomic DNA. Sequence B' in the set of splint oligonucleotides may be much less diverse because it simply serves as a locus identifier. As such, in the set of splint oligonucleotides, sequence B' may have a complexity of at least 2, e.g., 3 or 4, although sequence B' may have a complexity of at least 10, at least 100 or at least 1000 in some implementations. As would be apparent, because sequence B' is complementary to sequence B, the complexity of the set of locus-specific oligonucleotides may be the same as the complexity of sequence B'. For example, if there are three identifier oligonucleotides, there may be three different B' sequences. The number of splint oligonucleotides in a set may vary greatly, depending on the length of the locus and the number of target fragments. In some embodiments, each set of splint oligonucleotides may contain at least 10, at least 50, at least 100, at least 500, at least 1,000, at least 5,000, at least 10,000 or at least 50,000 different splint oligonucleotides.

For example, in some embodiments, a set of splint oligonucleotides may contain: (i) a first sub-population of splint oligonucleotides that contain least 100 A' sequences, e.g., set of $A_{1,\ x'}$, x=1-100+, which are complementary to different fragments of a first locus (e.g., fragments of chromosome 21 or, e.g., set of $A_{1,x}$, x=1-100+), where each of this sub-population of splint oligonucleotides have the same B' sequence, e.g., $B_1'$; (ii) a second sub-population of splint oligonucleotides that contain least 100 A' sequences, e.g., set of $A_{2,\ x'}$, x=1-100+, which are complementary to different fragments of a second locus (e.g., fragments of chromosome 18 or e.g., set of $A_{2\ x}$, x=1-100+), where each of this sub-population of splint oligonucleotides have the same B' sequence, e.g., $B_2'$, that is different from the B' sequence of the first (or any other) subpopulation; (iii) a third subpopulation of splint oligonucleotides that contain least 100 A' sequences, e.g., set of $A_{3,x'}$, x=1-100+, which are complementary to different fragments of a third locus (e.g., fragments of chromosome 18 or, e.g., set of $A_{3,x}$, x=1-100+), where each of this sub-population of splint oligonucleotides have the same B' sequence, e.g., $B_3'$, that is different from the B' sequence of the any other subpopulation; (iv) an optional fourth sub-population of splint oligonucleotides that contain least 100 A' sequences, e.g., set of $A_{4,x'}$, x=1-100+, which are complementary to different fragments of a fourth locus (e.g., fragments of another chromosome or, e.g., set of $A_{4,x}$, x=1-100+) where each of this subpopulation of splint oligonucleotides have a B' sequence, e.g., $B_4'$, that is different from the B' sequence of any other subpopulation.

Figure 3:
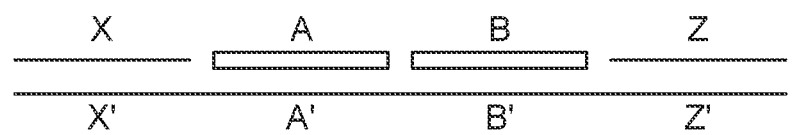
FIG. 3 schematically illustrates some exemplary probe system configurations.
Figure 3:
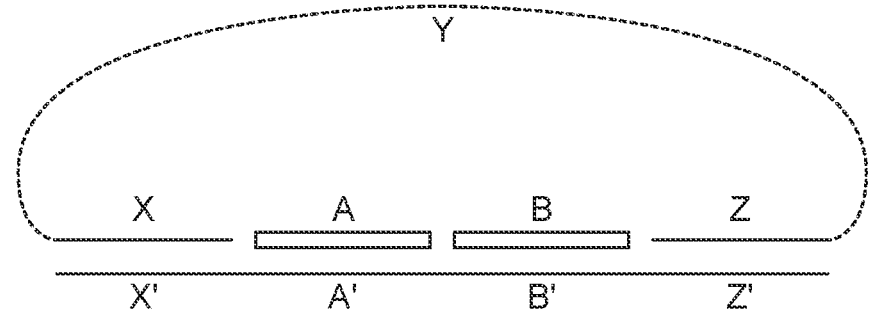
Figure 3:
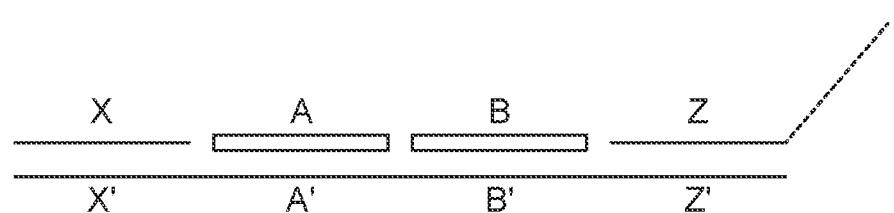
Figure 3:
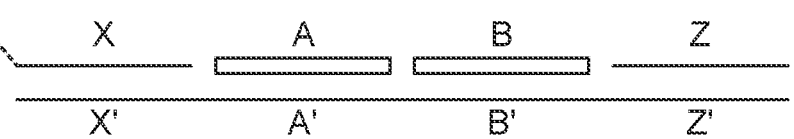
Figure 3:
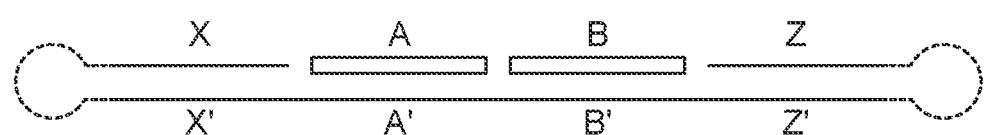

As illustrated in FIG. 3, the probe system may be configured in a variety of different ways depending on how it is going to be used. For example, as illustrated in FIGS. 3A, C and D, sequences X and Z may be in different molecules and, as a result the ligatable complex is linear. In these embodiments, the one or more probes that contain sequences X and Y may comprise a first oligonucleotide comprising sequence X and a second oligonucleotide comprising sequence Y. In these embodiments, the first and second oligonucleotides do not need to be tailed, as shown in FIG. 1A. In these embodiments, after ligation, the ligation products can be amplified using, e.g., talked PCR primers that hybridize to sequences X and Z. In some embodiments (as shown in FIGS. 3C and D), the first and/or second oligonucleotides may themselves have a tail to provide a primer binding site to facilitate amplification and counting. In some embodiments, a tail may contain a molecular indexer (e.g., a random sequence) that allows the number of original ligation products to be counted after those molecules have been amplified and sequenced. In alternative embodiments, and as shown in FIG. 3B, the one or more probes that contain sequences X and Y may be a single backbone probe of formula X-Y-Z. In these embodiments and as shown, the ligatable complex is a circular ligatable complex of formula X-A-B-Z-Y, where sequence Y joins sequences X and Z. In another embodiment illustrated in FIG. 3E, the one or more probes that contain sequences X and Z may be part of the splint oligonucleotide itself. In these embodiments, the ligation product may be a "dumbbell" shaped, as shown in FIG. 3E.

In these embodiments, the probe system may further comprising a pair of PCR primers that hybridize to the one or more probes that comprise sequences X and Z, thereby allowing the central part of the ligation product (i.e., the part that contains sequences A and B) to be amplified. In some embodiments, e.g., the embodiment shown in FIG. 3B, the probe system may further comprising a rolling circle amplification primer that hybridizes to a sequence in the backbone probe, thereby facilitating amplification of those products by rolling circle amplification. In some embodiments, the probe system may comprise a rolling circle amplification primer that hybridizes a sequence to the backbone probe, and up to four distinguishably labeled oligonucleotides, wherein each of the distinguishable labeled oligonucleotides hybridizes to the complement of a sequence B'. This will be explained in greater detail below.

As such, some embodiments of the probe system may comprise splint oligonucleotides, a backbone probe, and one or more locus-specific oligonucleotide. The probe system may also comprise one or more amplification primers, such as a rolling circle amplification primer that hybridizes a sequence in the backbone probe or a pair of PCR primers that hybridize to sites in the backbone probe, and, optionally, one or more labeled probes that hybridize to the complement of the locus-specific oligonucleotide.

As noted above, sequence A' varies between the different members of the set, and the sequences of A' are each designed to be complementary to a different target fragment of a genome. The sequences of A' may independently vary in length and sequence and, in some case, may be in the range of 8 to 80 nucleotides, e.g., 10 to 60 nucleotides, in length, depending on the length and sequence of the target fragments. Sequence B' identifies the locus from which the adjacent fragment is derived (e.g., a particular chromosome such as chromosome 18 or 21, etc.). Sequence B' may be of any suitable length, but in some embodiments it is in the range of 8 to 30 nucleotides in length. Within any single assay, sequences X' and Z' are different to one another, and are not variable. Sequence X' and Z' may be of any suitable length, but in some embodiments they are independently in the range of 8 to 30 nucleotides in length, although longer or shorter sequences can be used. The overall length of the splint oligonucleotides may be in the range of 50 to 200 nucleotides. In some embodiments, the splint oligonucleotides may be biotinylated, thereby allowing ligation products (discussed below) to be isolated from other, unligated, products prior to amplification. As would be apparent, sequences X and Z (which may be of any suitable length but in some embodiments they are independently in the range of 8 to 30 nucleotides in length) are not variable and hybridize to sequences X' and Z'. The locus-specific oligonucleotide is of sequence B which, again, may be of any suitable length, e.g., in the range of 8 to 30 nucleotides in length.

Figure 4:
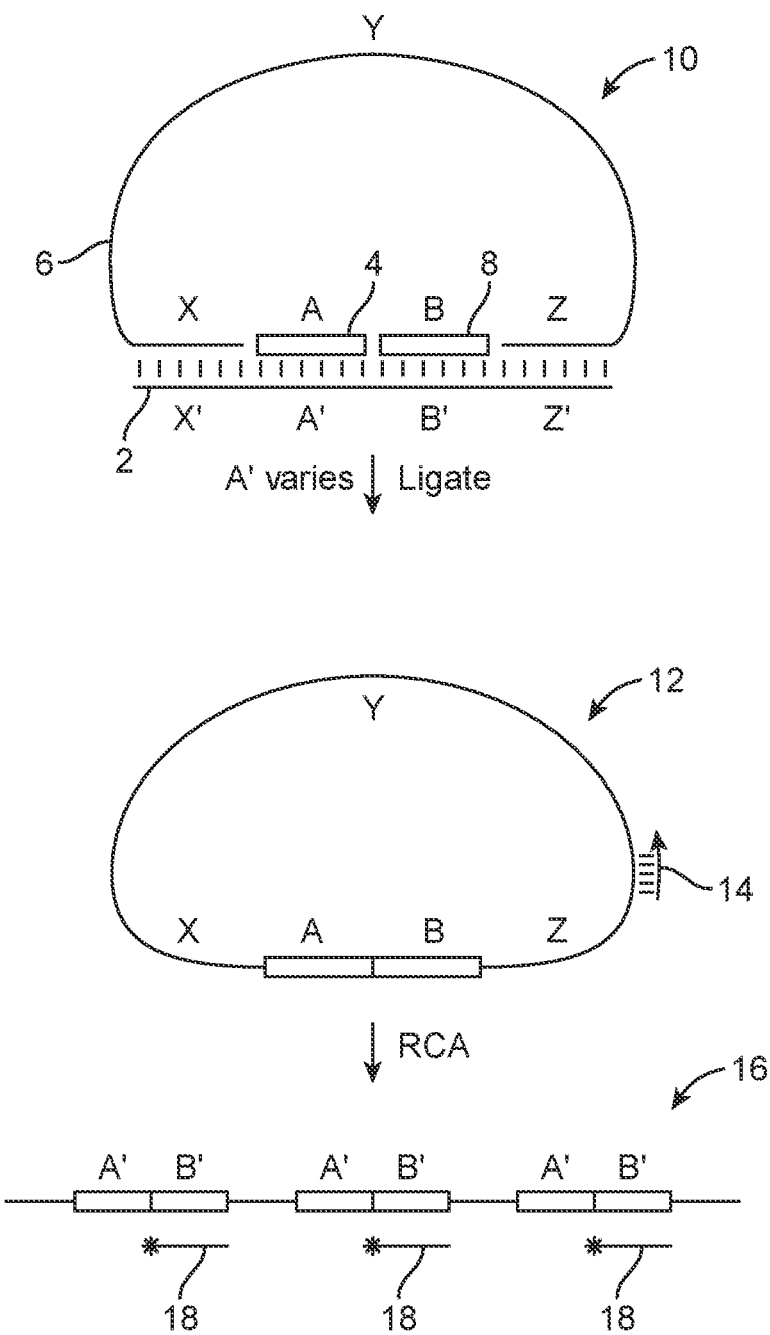
FIG. 4 schematically illustrates some of the features of an embodiment of a subject method.

As noted above, the complexes produced using the above-described probe system may be linear or circular (as shown in FIG. 3). FIG. 4 illustrates some of the features of the circular embodiment illustrated in FIG. 3B.

As shown in FIG. 4, in some embodiments, the probe system may comprise the set of splint oligonucleotides 2 (of formula X'-A'-B'-Z', which may be in the 5' to 3' or 3' to 5' orientation), a backbone probe 6 of formula X-Y-Z, where sequences X and Z are not variable and hybridize to sequences X' and Z' in an inverted orientation (i.e., so that the ends of the backbone are pointing toward one another, as shown), and a set of locus-specific oligonucleotides 8 is of sequence B. Sequence Y in the backbone probe may be any convenient length, e.g., 20 to 100 nucleotides. The overall length of backbone probe 6 may be in the range of 50 to 300 nucleotides in length, or longer in certain cases.

As shown in FIG. 4, the probe set is characterized in the various oligonucleotides can be hybridized with genomic fragments to produce a first set of ligatable circular complexes 10 (i.e., a complex in which the ends of the backbone probe 6, a locus-specific oligonucleotide 8 and a genomic fragment 4 are ligatably adjacent to one another and held ligatably adjacent to one another by a splint oligonucleotide 2). As shown in the illustrated example, the backbone probe 6, the locus-specific oligonucleotide 8 and the fragment 4 hybridize to the first splint oligonucleotides 2 to produce a set of ligatable circular complexes 10 of formula X-A-B-Z-Y, where sequence Y joins sequences X and Z. The fragments 4 that are present in this set of ligatable circular complexes 10 may be from at least 2, at least 5, at least 10, or at least 50 or more different loci (e.g., different chromosomes), and the identity of the locus from which an adjacent fragment is derived (e.g., the particular chromosomes) is provided by locus-specific oligonucleotide 8, which is the same sequence for each locus. In this example sequence A and A' (which correspond to the sequences of different genomic fragments) vary, B and B' (the locus identifier) vary, and sequences X, Y and Z do not vary.

As will be described in greater detail below, in this embodiment, the probe system (which comprises a first set of splint oligonucleotides 2, a backbone probe 6 and a locus-specific oligonucleotide 8) may be hybridized with a sample that comprises fragments of a genome 4 to produce a first set of ligatable circular complexes of formula X-A-B-Z-Y 10, as shown. After ligation of the ligatable circular complexes to produce a first set of circular DNA molecules 12 of formula X-A-B-Z-Y, the first set of circular DNA molecules can be amplified by rolling circle amplification (RCA) to produce a first set of RCA products 16. RCA may done using rolling circle amplification primer 14 that hybridizes a sequence in backbone probe 6, as illustrated in FIG. 4, or PCR primers that hybridize to sites that flank the ligated fragment. As such, in certain embodiments, the probe system may additionally comprise a rolling circle amplification primer 14, which primer hybridizes a sequence in backbone probe 6, or a pair of PCR primers that hybridize to sites that flank the ligated fragment. After RCA, the "source" of cloned fragment in a particular RCA product 16 (i.e., the locus, e.g., the particular chromosome, from which the cloned genomic fragment is derived) can then be determined by hybridizing a first labeled oligonucleotide 18 to the complement of sequence B (i.e., B'), or by sequencing. As would be apparent, labeled oligonucleotide 18 may comprise at least some of sequence B. As such, in certain embodiments, the probe system may additionally comprise a labeled oligonucleotide that hybridizes to the complement of first locus-specific oligonucleotide 8.

As would be apparent, if sequences from two or more different loci are to be detected in the same reaction, the probe system may comprise additional, distinguishably labeled oligonucleotides, one for each locus identifier B, so that both sets of RCA products can be identified at the same time. In these embodiments, the probe system may further comprise up to four distinguishably labeled oligonucleotides (e.g., $B_1$, $B_2$, $B_3$, $B_4$), where each of the distinguishable labeled oligonucleotides hybridizes to the complement of a sequence B' (e.g., $B_1'$, $B_2'$, $B_3'$, $B_4'$).

As would be apparent, the fragments to which the splint oligonucleotides hybridize are restriction fragments of the genome being analyzed. Further, any of the probes, oligonucleotides, or primers described above (e.g., the backbone probe) may contain a molecular barcode (e.g., an indexing sequence such as a random or semi-random sequence) such that each circular DNA molecule can be distinguished by the combination of the cloned fragment and the barcode, thereby allowing one to count how many initial molecules were sequenced, even after the molecules have been amplified (see, e.g., Casbon et al).

Methods

Also provide herein is a method comprising: (a) hybridizing a probe system as described above, with a test genomic sample that comprises fragments of a genome to produce ligatable complexes of formula X-A-B-Z; (b) ligating the ligatable complexes to produce product DNA molecules of formula X-A-B-Z; and (c) counting the product DNA molecules corresponding to each locus identifier of sequence B. In some embodiments, the counting may be done by sequencing the product DNA molecules, or amplification products thereof, to produce sequence reads, and counting the number of sequence reads comprising each sequence of B.

In embodiments in which the product DNA molecules are circular, the counting may comprise amplifying the product DNA molecules by rolling circle amplification, and counting the number amplification products comprising each sequence of B. In these embodiments, the method may comprise labelling the RCA products using distinguishably labeled probes that hybridize to sequence B, and the counting is done by counting the number of RCA products for each distinguishable label. The general principles of one implementation of this method are shown in FIG. 4. As would be apparent, the fragments to which the splint oligonucleotides hybridize can be (independently) top or bottom strands restriction fragments of the genome being analyzed. These fragments can be generated by digesting the genome with one or more restriction enzymes (e.g., a combination of enzymes that have a four base recognition sequence), and then denaturing the digested sample. As such, the fragments being cloned have defined ends, thereby allowing the design of splint oligonucleotides to clone those fragments. There are other ways to generate fragments that have defined ends (e.g., methods that use flap endonuclease, exonuclease, gap-fill, etc).

Figure 5:
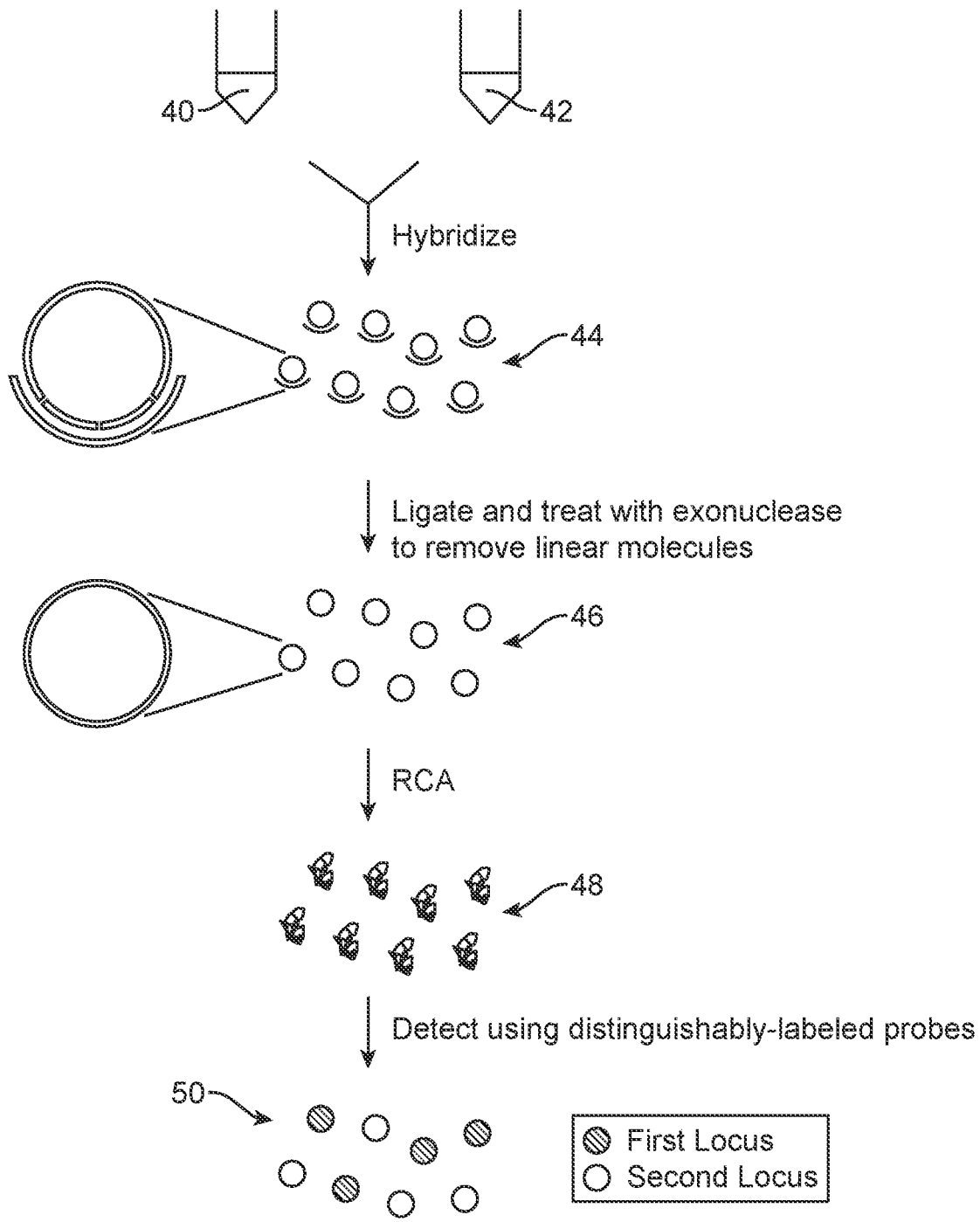
FIG. 5 schematically illustrates some of the features of one implementation of a subject method.

As indicated above, this method may be multiplexed to provide a way to analyze two or more different loci, as shown in FIG. 5. With reference to FIG. 5, a sample containing fragments of genomic DNA 40 may be: a) hybridized with a probe system 42 comprising: (i) a first set of splint probes, as described above; (ii) a first-locus specific oligonucleotide, as described above; (iii) a second set of splint probes, as described above; (iv) a second locus-specific oligonucleotide, as described above; and, (v) a backbone probe, as described above, to produce a mixture 44 comprising first set of ligatable circular complexes of formula X-A-B-Z-Y (which contain fragments from the first locus, e.g., a first chromosome, as well as fragments from a second locus, e.g., a second chromosome). Next, the method comprises (b) ligating the ligatable circular complexes to produce a mixture of circular DNA molecules 46 (which contains the first and second sets of circular DNA molecules), and, after treating the sample with an exonuclease to remove linear nucleic acid molecules, (c) amplifying the circular DNA molecules 46 by rolling circle amplification using a single primer that hybridizes to the backbone probe, to produce RCA products 48. The locus from which each of the fragments contained within each RCA product can then be identified by hybridizing the RCA products to distinguishably labeled first and second oligonucleotide probes, which hybridize to the complement of the locus-specific oligonucleotide that is present in each of the products, to produce a labeled sample 50. In these embodiments, the method may comprise: (d) separately detecting: (i) RCA products that contain fragments from a first locus using a labeled probe that hybridizes to a first locus identifier sequence and (ii) RCA products that contain fragments from a second locus using a labeled probe that hybridizes to a second locus identifier sequence, wherein the labeled probes are distinguishably labeled. As noted above, after ligation, if the splint oligonucleotides are biotinylated the circular products may be isolated from unligated products using, e.g., streptavidin beads. In either event, the ligated sample may be treated with an exonuclease, thereby removing linear DNA molecules from the reaction. This principle may be expanded to count to the number of ligation products produced for any number of loci (e.g., 3, 4, up to 10 or up to 100 or more loci).

In some embodiments, the detecting step may (d) comprise: (i) depositing the RCA products on a support; and, (ii)

separately counting the number of the individual labeled RCA products that are labeled with one label and the number of individual labeled RCA products labeled with another label in an area of the support. As would be understood, hybridization of the labeled oligonucleotides may be done before the RCA products are distributed on the support, or after the RCA products are distributed on the support.

In other words, the number of rolling circle amplification products corresponding to each locus can be estimated by, e.g., distributing the RCA products on the surface of a support (a slide or porous membrane), hybridizing the RCA products using labelled oligonucleotides (e.g., fluorescently labelled oligonucleotides) and then counting the number of discrete signals in an area of the support, e.g., using a fluorescence reader. The labelling can be done before or after the products have been distributed on the support and, because each RCA product contains thousands of copies of the same sequences, there should be thousands of binding sites for the labelled oligonucleotides, thereby increasing the signal. In multiplex embodiments (e.g., in which RCA products corresponding to two different locus are being counted), the RCA products corresponding to one locus can be labelled with one fluorophore and the RCA products corresponding to another locus can be labelled with a different fluorophore, thereby allowing the different RCA products to be separately counted.

In certain embodiments, the method may comprise (a) filtering a liquid sample containing the rolling circle amplification (RCA) products through a porous transparent capillary membrane, thereby concentrating the RCA products and producing an array of the RCA products on the membrane; (b) fluorescently labeling the RCA products prior to or after step (a); and, (c) counting the number of the individual labeled RCA products in an area of the membrane, thereby providing an estimate of the number of the labeled RCA products in the sample. In some embodiments, the porous transparent capillary membrane may be a porous anodic aluminum oxide membrane. In these embodiments, the labeling step (b) may done by hybridizing fluorescently labeled oligonucleotides to the RCA products, prior to or after step (a). In certain embodiments, the method may comprise imaging an area of the membrane to produce one or more images and counting the number of the individual labeled RCA products in the one or more images. Examples of such methods are described in PCT/IB2016/052495, filed on May 2, 2016, which is incorporated by reference herein.

Quantifying signals from individual RCA products is significant because, in many applications (e.g., non-invasive pre-natal diagnosis by analysis of cfDNA), the number of fragments corresponding to particular chromosomes (e.g., chromosome 21) needs to be determined quire accurately and without bias. Typical analysis methods use PCR which, as is well known, is a very biased procedure in that some sequences are amplified much higher efficiencies than others. This makes PCR-based strategies impractical for many diagnostic efforts.

In particular embodiments, the sample may contain multiple populations of RCA products (e.g., two, three or four or more populations of RCA products such as a first population of labeled RCA products and a second population of RCA products), where the different populations of RCA products are distinguishably labeled, meaning that the individual members of each of the populations of RCA products labels can be independently detected and counted, even when the populations are mixed. Suitable distinguishable fluorescent label pairs useful in the subject methods include, e.g., Cy-3 and Cy-5 (Amersham Inc., Piscataway, NJ), Quasar 570 and Quasar 670 (Biosearch Technology, Novato CA), Alexafluor555 and Alexafluor647 (Molecular Probes, Eugene, OR), BODIPY V-1002 and BODIPY V1005 (Molecular Probes, Eugene, OR), POPO-3 and TOTO-3 (Molecular Probes, Eugene, OR), and POPRO3 TOPRO3 (Molecular Probes, Eugene, OR). Further suitable distinguishable detectable labels may be found in, e.g., Kricka et al. (Ann Clin Biochem. 39:114-29, 2002). For example, the RCA products may be labeled with any combination of ATTO, ALEXA, CY, or dimeric cyanine dyes such as YOYO, TOTO etc. Other labels may also be used.

In some cases, a population of RCA products can be distinguishably labeled by labeling it with multiple labels, thereby increasing the possibilities of multiplexing. For example, in some cases a population may be labeled with two distinguishable dyes (e.g., Cy3 and Cy5), which, when read, will be distinguishable from populations that are labeled with the individual dyes (e.g., Cy3 or Cy5). In some embodiments, a first population of RCA products represent a "test" population of labeled RCA products and a second population of RCA products represent a "reference" population of RCA products to which the number of the first RCA products can be compared. For example, in some embodiments, a first population of RCA products may correspond to a first chromosomal region (e.g., a first chromosome such as chromosome 21) and a second population of RCA products may correspond to a second chromosomal region (e.g., a second chromosome such as chromosome 13 or 18 or a different region of the first chromosome) and the number of the first population of RCA products and the second population of RCA products can be counted and compared to determine if there is a difference in the copy number of the regions (indicating that there is duplication or deletion of the test region). In some embodiments, the sample contains at least a first population of RCA products and a second population of RCA products, wherein the first and second populations of labeled RCA products are distinguishably labeled in the labeling step (step (b)). In these embodiments, the method comprises counting the number of first labeled RCA products in an area of the membrane and counting the number of second labeled RCA products in an area (the same area or a different area) of the membrane, thereby providing an estimate of the number of first and second populations of RCA products in the sample. This embodiment may further involve comparing the number of first RCA products in the sample to the number of second RCA products in the sample.

In some of these embodiments of the method, the method may comprise imaging the first and second populations of labeled RCA products to produce one or more images (e.g., a first image and a second image, respectively) and, optionally, (i) counting the number of labeled RCA products in the one or more images, thereby providing an estimate of the number of first and second populations of labeled RCA products in the sample. The first and second populations of labeled RCA products can be separately detected using known methods (e.g., using appropriate filters etc.). These embodiments of the method may further comprise comparing the number of first labeled RCA products in the sample to the number of second labeled RCA products in the sample. This step of the method may involve counting at least 1,000 (e.g., at least 5,000, at least 10,000, at least 20,000, at least 50,000, at least 100,000, at least 500,000 up to 1M or more) labeled RCA products in the first population at least 1,000 (e.g., at least 5,000, at least 10,000, at least 20,000 or at least 50,000, at least 100,000, at least 500,000 up to 1M or more) labeled RCA products in an area of the membrane and counting, thereby ensuring that a difference in copy number can be called with statistical rigor.

In alternative embodiments, cloned fragments in the DNA molecules (and, optionally, any indexing sequence in the circular DNA molecules) may be amplified by PCR using PCR primers that hybridize to or are the same as sites that flank those sequences. In this embodiment, a PCR product can be amplified using the primers. In this embodiment, the amount of the product can be quantifying by any suitable qPCR assay, e.g., a TaqMan assay or the like. In another embodiment, the product may be sequenced (with or without amplification). In these embodiments, the amount of circular molecules corresponding to each locus can be estimated by counting the number of sequence reads corresponding to the locus (e.g., counting how many sequence reads have a particular locus-specific barcode sequence). In some embodiments, if an indexing sequence is used, the number of circular molecules corresponding to each locus can be counted by determining how many different molecular barcode sequences are associated with each locus-specific barcode sequence As would be apparent, in this embodiment, the primers used may contain sequences that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps.

The test genomic sample may be from a patient that is suspected or at risk of having a disease or condition, and the results of step (c) an indication of whether the patient, or fetus thereof, has the disease or condition. In some embodiments, the disease or condition may be a cancer, an infectious disease, an inflammatory disease, a transplant rejection, or a chromosomal defect such as a trisomy.

As noted above, in some cases the sample being analyzed using this method may be a sample of cfDNA obtained from blood, e.g., from the blood of a pregnant female. In these embodiments, the method may be used to detect chromosome abnormalities in the developing fetus (as described above) or to calculate the fraction of fetal DNA in the sample, for example.

Illustrative copy number abnormalities that can be detected using the method include, but are not limited to, trisomy 21, trisomy 13, trisomy 18, trisomy 16, XXY, XYY, XXX, monosomy X, monosomy 21, monosomy 22, monosomy 16, and monosomy 15. Further copy number abnormalities that can be detected using the present method are listed in the following table.

| Chromosome | Abnormality and Disease Association |
|---|---|
| X: | XO (Turner's Syndrome) |
| Y: | XXY (Klinefelter Syndrome) |
| Y: | XYY (Double Y Syndrome) |
| Y: | XXX (Trisomy X Syndrome) |
| Y: | XXXX (Four X Syndrome) |

-continued

| Chromosome | Abnormality and Disease Association |
|---|---|
| Y: | Xp21 deletion (Duchenne's/Becker Syndrome, congenital adrenal hypoplasia, chronic granulomatus disease) |
| Y: | Xp22 deletion (steroid sulfatase deficiency) |
| Y: | Xq26 deletion (X-linked lymphoproliferative disease) |
| 1: | 1p somatic (neuroblastoma) |
| 1: | monosomy (neuroblastoma) |
| 1: | trisomy (neuroblastoma) |
| 2: | monosomy (growth retardation, developmental and mental delay, and minor physical abnormalities) |
| 2: | trisomy 2q (growth retardation, developmental and mental delay, and minor physical abnormalities) |
| 3: | monosomy (Non-Hodgkin's lymphoma) |
| 3: | trisomy somatic (Non-Hodgkin's lymphoma) |
| 4: | monosomy (Acute non lymphocytic leukemia (ANLL)) |
| 4: | trisomy somatic (Acute non lymphocytic leukemia (ANLL)) |
| 5: | 5p (Cri du chat; Lejeune syndrome) |
| 5: | 5q somatic (myelodysplastic syndrome) |
| 5: | monosomy (myelodysplastic syndrome) |
| 5: | trisomy (myelodysplastic syndrome) |
| 6: | monosomy (clear-cell sarcoma) |
| 6: | trisomy somatic (clear-cell sarcoma) |
| 7: | 7q11.23 deletion (William's syndrome) |
| 7: | monosomy (monosomy 7 syndrome of childhood; somatic: renal cortical adenomas; myelodysplastic syndrome) |
| 7: | trisomy (monosomy 7 syndrome of childhood; somatic: renal cortical adenomas; myelodysplastic syndrome) |
| 8: | 8q24.1 deletion (Langer-Giedon syndrome) |
| 8: | monosomy (myelodysplastic syndrome; Warkany syndrome; somatic: chronic myelogenous leukemia) |
| 8: | trisomy (myelodysplastic syndrome; Warkany syndrome; somatic: chronic myelogenous leukemia) |
| 9: | monosomy 9p (Alfi's syndrome) |
| 9: | monosomy 9p (Rethore syndrome) |
| 9: | partial trisomy (Rethore syndrome) |
| 9: | trisomy (complete trisomy 9 syndrome; mosaic trisomy 9 syndrome) |
| 10: | monosomy (ALL or ANLL) |
| 10: | trisomy somatic (ALL or ANLL) |
| 11: | 11p- (Aniridia; Wilms tumor) |
| 11: | 11q- (Jacobsen Syndrome) |
| 11: | monosomy (myeloid lineages affected (ANLL, MDS)) |
| 11: | trisomy somatic (myeloid lineages affected (ANLL, MDS)) |
| 12: | monosomy (CLL, Juvenile granulosa cell tumor (JGCT)) |
| 12: | trisomy somatic (CLL, Juvenile granulosa cell tumor (JGCT)) |
| 13: | 13q- (13q-syndrome; Orbeli syndrome) |
| 13: | 13q14 deletion (retinoblastoma) |
| 13: | monosomy (Patau's syndrome) |
| 13: | trisomy (Patau's syndrome) |
| 14: | monosomy (myeloid disorders (MDS, ANLL, atypical CML) |
| 14: | trisomy somatic (myeloid disorders (MDS, ANLL, atypical CML) |
| 15: | 15q11-q13 deletion (Prader-Willi, Angelman's syndrome) |
| 15: | monosomy (Prader-Willi, Angelman's syndrome) |
| 15: | trisomy somatic (myeloid and lymphoid lineages affected, e.g., MDS, ANLL, ALL, CLL) |
| 16: | 16q13.3 deletion (Rubenstein-Taybi) |
| 16: | monosomy (papillary renal cell carcinomas (malignant)) |
| 16: | trisomy somatic (papillary renal cell carcinomas (malignant)) |
| 17: | 17p- somatic (17p syndrome in myeloid malignancies) |
| 17: | 17q11.2 deletion (Smith-Magenis) |
| 17: | 17q13.3 (Miller-Dieker) |
| 17: | monosomy (renal cortical adenomas) |
| 17: | trisomy somatic (renal cortical adenomas) |
| 17: | 17p11.2-12 (Charcot-Marie Tooth Syndrome type 1; HNPP) |
| 17: | trisomy (Charcot-Marie Tooth Syndrome type 1; HNPP) |
| 18: | 18p- (18p partial monosomy syndrome or Grouchy Lamy Thieffry syndrome) |
| 18: | 18q- (Grouchy Lamy Salmon Landry Syndrome) |

| Chromosome | Abnormality and Disease Association |
|---|---|
| 18: | monosomy (Edwards syndrome) |
| 18: | trisomy (Edwards syndrome) |
| 19: | monosomy (Edwards syndrome) |
| 19: | trisomy (Edwards syndrome) |
| 20: | 20p- (trisomy 20p syndrome) |
| 20: | 20p11.2-12 deletion (Alagille) |
| 20: | 20q- (somatic: MDS, ANLL, polycythemia vera, chronic neutrophilic leukemia) |
| 20: | monosomy (papillary renal cell carcinomas (malignant)) |
| 20: | trisomy somatic (papillary renal cell carcinomas (malignant)) |
| 21: | monosomy (Down's syndrome) |
| 21: | trisomy (Down's syndrome) |
| 22: | 22q11.2 deletion (DiGeorge's syndrome, velocardiofacial syndrome, conotruncal anomaly face syndrome, autosomal dominant Opitz G/BBB syndrome, Caylor cardiofacial syndrome) |
| 22: | monosomy (complete trisomy 22 syndrome) |
| 22: | trisomy (complete trisomy 22 syndrome) |

The method described herein can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, where in certain embodiments the mammal is a human. In exemplary embodiments, the genomic sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cfDNA obtained from blood, e.g., from the blood of a pregnant female.

For example, in some embodiments, a sample of DNA may be obtained and the sample digested with one or more restriction enzymes (or a RNA-guided endonuclease such as cas9) to produce predictable fragments (the median size of which may be in the range of 20-100 bases). The method described above may be performed on the digested DNA, and the number of fragments corresponding one locus (e.g., one chromosome) can be compared to the number of fragments corresponding to another locus (e.g., another chromosome) using the method described herein. As noted, the method may be used to identify copy number differences, e.g., chromosome aneuploidies, that are associated with a disease or condition.

As noted above, in some cases the sample analyzed may be a sample of cfDNA obtained from blood, e.g., from the blood of a pregnant female. In these embodiments, the method may be used to detect chromosome abnormalities in the developing fetus or to calculate the fraction of fetal DNA in the sample, for example.

Kits

Also provided by this disclosure are kits for practicing the subject methods, as described above. In certain embodiments, the kit may comprise: (a) a set of splint oligonucleotides of formula X'-A'-B'-Z', wherein: within the set: (i) the sequence of A' and B' vary, and (ii) the sequences of X' and Z' are different to each other and are not variable; and within each molecule: (i) sequence A' is complementary to a fragment of a genome and (ii) sequence B' identifies the locus from which the genomic fragment that hybridizes to the adjacent A' sequence is derived; (b) one or more probes comprising sequences X and Z, wherein: i. sequences X and Z are not variable and hybridize to sequence X' and Z'; and (c) a set of locus-specific oligonucleotides of sequence B; and wherein: each splint oligonucleotide of (a) is capable of hybridizing to (i) the probe sequences of (b); (ii) a locus-specific oligonucleotide of (c); and, (iii) a genomic fragment of (a), to produce a ligatable complex of formula X-A-B-Z, in which sequence B identifies the locus of adjacent sequence A. In some embodiments, the one or more probes of (b) comprise a first oligonucleotide comprising sequence X and a second oligonucleotide comprising sequence Y. In some embodiments, the kit may further comprise a pair of PCR primers that hybridize to the one or more probes comprising sequences X and Y. In certain embodiments, the one or more probes of (b) is a backbone probe of formula X-Y-Z, and the ligatable complex is a circular ligatable complex of formula X-A-B-Z-Y, where sequence Y joins sequences X and Z, and sequence B identifies the locus of adjacent sequence A In these embodiments, the kit may further comprise a rolling circle amplification primer that hybridizes to a sequence in the backbone probe. In these embodiments, the kit may comprise a plurality of distinguishably labeled oligonucleotides, wherein each of the distinguishable labeled oligonucleotides hybridizes to the complement of a B' sequence. The kit may additionally contain a ligase and/or a strand-displacing polymerase for performing rolling circle amplification.

The various components of the kit may be present in separate containers or certain compatible components (e.g., the first and second sets of splint probes and the first and second locus-specific probes) may be precombined into a single container, as desired.

In addition to the above-mentioned components, the subject kit may further include instructions for using the components of the kit to practice the subject method.

EXAMPLES

The following examples are put forth so as to provide those of ordinary skill in the art with additional disclosure and description of how to make and use the present invention, and are not intended to limit the scope of what the inventors regard as their invention nor are they intended to represent that the experiments below are all or the only experiments performed.

Example I

Initial Data Validating Method

Figure 6:
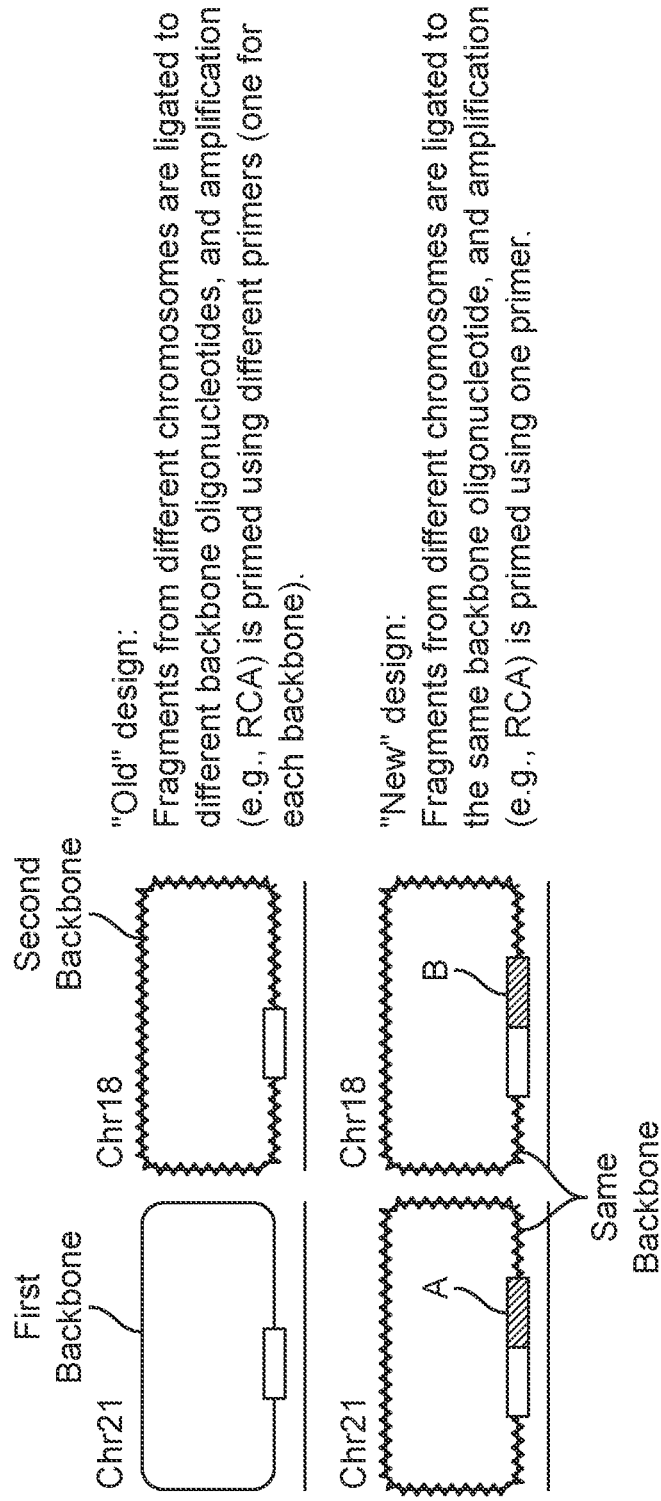
FIG. 6 schematically illustrates the design of probe systems.

The purpose of this experiment is to compare the methods that use backbone oligonucleotides that are chromosome-specific (e.g., the backbone oligonucleotide used to capture fragments from a first chromosome, e.g., chromosome 21, is different from the backbone oligonucleotide used to capture fragments from a second chromosome, e.g., chromosome 18, as described in described in WO2015083001 and WO2015083002), with methods in which the same backbone oligonucleotide is used for all chromosomes examined. This is illustrated in FIG. 6. As shown, in the "new" design, the source of a cloned fragment is determined using a chromosome-specific sequence (e.g., A or B) that is cloned into the same circular product as the target fragment. In the new method, a single backbone oligonucleotide is used (compared to multiple backbone oligonucleotides in the prior method), and the cloned fragments from all chromosomes can be amplified using the same RCA primer or a single pair of PCR primers.

Cell-line DNA (10 ng) was digested denatured and hybridized to the "old" and "new" probe designs. Following hybridization and ligation, the ligation reactions were subjected to exonuclease treatment to remove any non-circularized DNA in the solution. The remaining circular products served as templates in an RCA reaction, which produced concatemeric copies of the circular products. These RCA products were labeled with fluorescently labeled oligonucleotides complementary to the "splint" sequence, and deposited to a solid support for detection.

Thirteen cfDNA samples from pregnant women were subjected to the same reaction as described above.

For all reactions, the number of individual objects (RCA products) was counted in each color. The ratio of the number of objects in color A/B was calculated for each sample and the coefficient of variation was calculated as a measure of precision of the assay. Low coefficient of variation enables precise measurements of samples with low fetal fraction. This was illustrated by adding samples containing a low spike-in amount of trisomy 21 cell-line sample.

Figure 7:
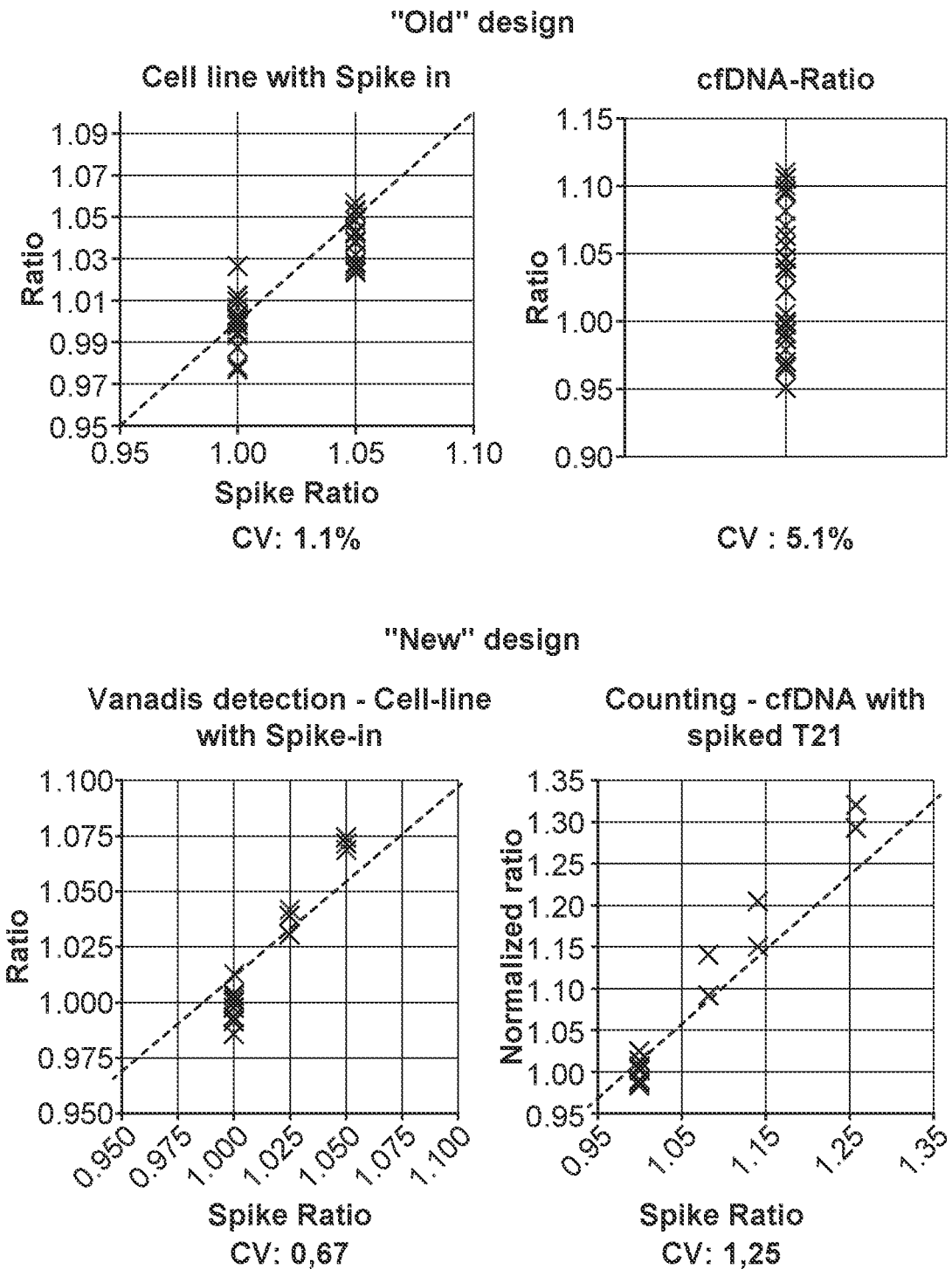
FIG. 7 shows data obtained using two different probe systems.
Figure 8:
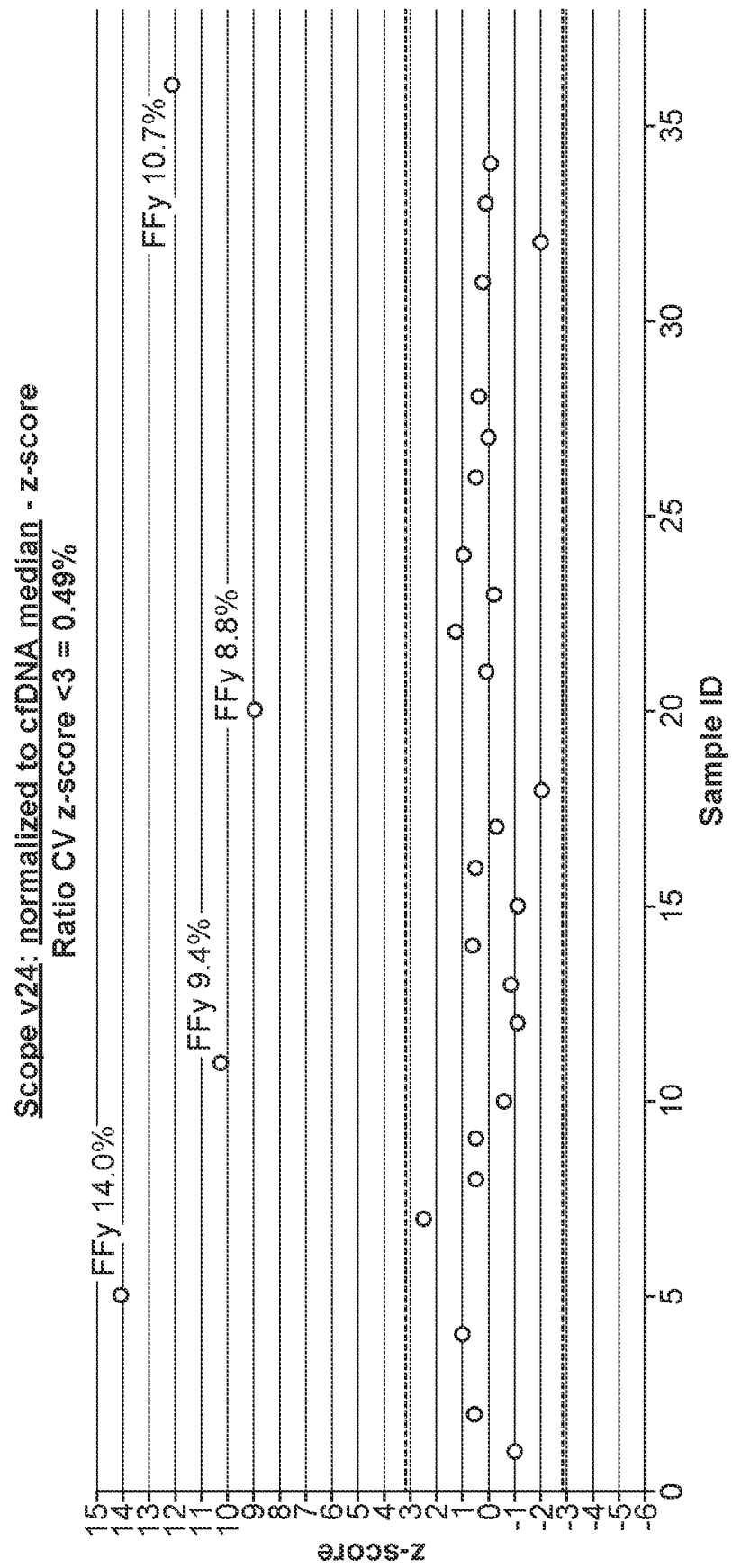
FIG. 8 shows data obtained from the analysis of clinical samples.

According to the data shown in FIG. 7, the new design generates a lower CV for both cell-line DNA and cfDNA, enabling a more accurate measurement of fetal DNA with chromosomal abnormalities.

Without wishing to be bound to any particular theory, it is believed that this method may be less sensitive for impurities in the sample.

Example II

Analysis of Clinical Samples cfDNA samples from 26 normal pregnant individuals and 4 individuals carrying a fetus with trisomy 21 was prepared. Blood (10 ml) from each patent were centrifuged to separate plasma from red blood cells and buffy coat. The corresponding plasma (~3-5 ml/patient) was subjected to a bead-based DNA extraction protocol, resulting in extracted cfDNA diluted in 50 ul of buffer.

The cfDNA was then subjected to the method herein described above and analyzed by digital counting of rolling-circle products using fluorescence microscope. All 4 positive cases were detected above a z-score above 3. The CV of the normal samples was calculated to 0.49% demonstrating the high precision of the assay.

The invention claimed is:

1. A ligatable nucleic acid complex of formula X-A-B-Z or X-B-A-Z, wherein, in the complex:
   sequences A and B are in separate molecules,
   sequences X, A, B and Z are ligatably adjacent to one another and held in position by a splint oligonucleotide,
   sequence A is a target fragment of a genome,
   sequence B identifies the locus from which the adjacent sequence A is derived but is not from the locus, and
   the splint oligonucleotide is of formula X'-A'-B'-Z' or X'-B'-A'-Z'.

2. The ligatable complex of claim 1, wherein sequence A is a target fragment of the human genome.

3. The ligatable complex of claim 1, wherein the target fragment is strand of restriction fragment.

4. The ligatable complex of claim 1, wherein sequence B identifies a region on a chromosome.

5. The ligatable complex of claim 1, wherein sequence B identifies a particular chromosome arm.

6. The ligatable complex of claim 1, wherein sequence B identifies a particular chromosome.

7. The ligatable complex of claim 1, wherein sequence B indicates that the adjacent sequence A is from chromosome 21.

8. The ligatable complex of claim 1, wherein the complex is a circular ligatable complex of formula X-A-B-Z-Y, where sequence Y joins sequences X and Z.

9. The ligatable complex of claim 1, wherein the complex is linear.

10. The ligatable complex of claim 1, wherein the splint oligonucleotide is of formula X'-A'-B'-Z' or X'-B'-A'-Z' and wherein sequence A' is in the range of 8 to 80 nucleotides.

11. The ligatable complex of claim 1, wherein the splint oligonucleotide is of formula X'-A'-B'-Z' or X'-B'-A'-Z' and wherein sequence B' is in the range of 8 to 30 nucleotides in length.

12. The ligatable complex of claim 1, wherein, sequences X and Z are independently in the range of 8 to 30 nucleotides in length.

* * * * *